(12) United States Patent
Bertrand et al.

(10) Patent No.: US 7,607,213 B2
(45) Date of Patent: Oct. 27, 2009

(54) METHOD OF MAKING A DEVICE FOR MEASURING DEFORMATION

(75) Inventors: Pierre Bertrand, Montbelliard (FR); Christian Coddet, Giromagny (FR); Sophie Costil, Offemont (FR); Frederic Leman, Montrouge (FR); Sebastien Lukat, Mulhouse (FR)

(73) Assignee: SNECMA, Paris (FR)

( * ) Notice: Subject to any disclaimer, the term of this patent is extended or adjusted under 35 U.S.C. 154(b) by 0 days.

(21) Appl. No.: 12/109,042

(22) Filed: Apr. 24, 2008

(65) Prior Publication Data

US 2008/0264176 A1   Oct. 30, 2008

(30) Foreign Application Priority Data

Apr. 30, 2007   (FR) .................................... 07 54789

(51) Int. Cl.
*H01S 4/00*       (2006.01)
*G01R 31/00*      (2006.01)

(52) U.S. Cl. ........................... 29/592.1; 29/593; 29/595; 29/25.35; 438/50; 438/960

(58) Field of Classification Search ................ 29/592, 29/593, 594, 620, 621.1, 25.35–25.42; 73/800, 73/862.041, 861.52; 438/50, 543, 546, 960; 72/53; 156/345.51
See application file for complete search history.

(56) References Cited

U.S. PATENT DOCUMENTS

| | | | | |
|---|---|---|---|---|
| 3,750,270 | A * | 8/1973 | Ishii ........................... | 438/50 |
| 5,867,886 | A * | 2/1999 | Ratell et al. .................. | 29/595 |
| 6,299,988 | B1 | 10/2001 | Wang et al. | |
| 7,442,444 | B2 * | 10/2008 | Hazel et al. ................. | 428/641 |

FOREIGN PATENT DOCUMENTS

| | | |
|---|---|---|
| GB | 893571 | 4/1962 |
| JP | 9-159170 | 6/1997 |

OTHER PUBLICATIONS

U.S. Appl. No. 12/108,867, filed Apr. 24, 2008, Leman et al.

* cited by examiner

*Primary Examiner*—Minh Trinh
(74) *Attorney, Agent, or Firm*—Oblon, Spivak, McClelland, Maier & Neustadt, L.L.P.

(57) ABSTRACT

A method of making a device for measuring deformation includes a step of depositing a silicon adhesion underlayer on a silicon carbide surface by chemical vapor spraying, and a step of depositing a coating on the silicon adhesion underlayer by atmospheric thermal spraying.

4 Claims, 1 Drawing Sheet

METHOD OF MAKING A DEVICE FOR MEASURING DEFORMATION

The present invention relates to a method of depositing an alumina coating on a part having its surface made of silicon carbide (SiC).

BACKGROUND OF THE INVENTION

The part may be a solid SiC part, or a part having a substrate that is not made of SiC and that is covered in an SiC layer. Parts comprising a substrate covered in an SiC layer are used in high temperature applications, i.e. applications for temperatures in the range 300° C. to 1100° C. By way of example, the substrate may be a ceramic matrix composite (CMC), i.e. a ceramic matrix reinforced by ceramic or carbon fibers, for example. The SiC layer is to give the part better resistance to oxidation and better mechanical properties at high temperatures. Because of these properties, such parts are used in particular in aviation turbomachines.

In certain applications, it is necessary for the SiC surface to have deposited thereon a coating, e.g. of metal or ceramic, such as mullite, cordierite, or zirconia. The coating is generally for the purpose of improving the high temperature strength or resistance to corrosion of the part on which it is deposited. Deposition can be performed either by atmospheric thermal spraying, or by means of a cement.

Typically, said coating is of alumina $Al_2O_3$. Alumina is deposited either by atmospheric thermal spraying of alumina (atmospheric plasma spraying of powder or flame spraying of a wire), or else in the form of an alumina-based cement, or indeed by a combination of those methods, which are well known in the state of the art.

Mechanical and thermal tests performed on parts having an SiC surface covered in an alumina coating show that the main mode of failure is rupture at the interface between the SiC surface and the alumina coating.

In order to improve the tenacity of the interface, modifications have been made to the state of the SiC surface. Thus, sand blasting (using compressed air to blow particles of alumina having a diameter of a few hundreds of micrometers) has been performed on the SiC surface in order to increase its roughness. Nevertheless, sand blasting leads to damage to the SiC surface without creating favorable roughness.

The present invention seeks to remedy those drawbacks.

OBJECTS AND SUMMARY OF THE INVENTION

The invention seeks to provide a method of making an alumina coating on a part having a silicon carbide (SiC) surface, that enables the tenacity of the interface between the SiC surface and the alumina coating to be improved.

This object is achieved by the fact that the method comprises the following steps:

a) depositing a silicon adhesion underlayer on the SiC surface by chemical vapor spraying; and b) depositing a coating on the silicon adhesion underlayer by atmospheric thermal spraying.

By means of these provisions, the alumina coating is deposited on a surface (the silicon underlayer) that presents greater roughness than the SiC surface, thereby enhancing mechanical anchoring of the alumina coating. In addition, alumina has better physicochemical affinity with silicon than with SiC. Furthermore, the good match between the coefficients of expansion of silicon and of SiC serves to minimize mechanical stresses at the silicon/SiC interface during heat stressing. Thus, the interface between the part and the alumina coating withstands high temperatures better.

Parts having the substrate covered in a layer of silicon carbide (SiC) are commonly used in high temperature applications as mentioned above. It is necessary to optimize the dimensioning of said parts, for reasons of size, weight, and expense. This dimensioning is performed in particular by laboratory testing or by testing under working conditions, during which deformations of such parts under thermomechanical stressing are studied. In order to be able to measure such deformations, use is made of strain gauges, typically free filament gauges (it is also possible to thin layer gauges, but their complex deposition techniques make them used less widely). Such gauges comprise an alloy filament that is fastened on the part. When the part deforms, the filament is stretched or contracted, thereby leading to a corresponding variation in its electrical resistivity. By passing a current through the filament, it is possible, in real time, to measure the variations in the electrical resistivity of the filament, and as a result to measure the deformations of the part on which it is fastened. In order to measure such deformations effectively, it is essential to ensure that the gauge adheres securely to the surface of the part, so that deformations of the surface of the part are transmitted effectively to the gauge. Typically, the gauge is placed on a first alumina coating previously deposited on the part, and then the gauge and said first coating are covered in an additional alumina coating that holds the gauge in intimate contact with the first coating.

Nevertheless, it can happen that the first coating separates from the surface of the part, so the gauge does not act effectively in measuring the deformation of the surface of the part, and the measurements taken are not reliable. As mentioned above, for parts having a substrate covered in SiC and that are covered in an alumina coating of the state of the art, delamination can occur at high temperatures at the part/coating interface. Such delamination occurs even when the SiC layer has been subjected to sand blasting. It is therefore necessary to improve the adhesion between the first ceramic coating and the SiC layer, and thus with the underlying part. This improved adhesion is obtained by depositing an adhesion underlayer of silicon on the SiC layer by vacuum plasma spraying, as mentioned above.

Consequently, the invention also provides a method of making a device for measuring deformation of a substrate covered in an SiC layer deposited by chemical vapor deposition, the method comprising the following steps:

a) depositing an adhesion underlayer of silicon on the SiC layer by vacuum plasma spraying;

b) depositing an alumina coating on the silicon adhesion underlayer by atmospheric thermal spraying;

c) placing a free filament strain gauge on the alumina coating, the gauge being held on its support, and the support possessing openings;

d) depositing a second alumina coating on the strain gauge and on the coating by atmospheric thermal spraying through said openings;

e) removing the support; and f) depositing a third alumina coating by atmospheric thermal spraying on the coating, on the second coating, and on the strain gauge.

The invention also provides a device for measuring deformation of a part constituted by a substrate covered in a layer of silicon carbide, SiC, deposited by chemical vapor deposition.

According to the invention, the device comprises a first coating of alumina deposited by atmospheric thermal spraying onto a silicon adhesion underlayer deposited on said silicon carbide layer by vacuum plasma spraying, a free filament strain gauge disposed on said first coating, and an additional coating of alumina deposited by atmospheric thermal spraying on said strain gauge.

By means of these provisions, the first alumina coating is deposited on a surface (silicon underlayer) presenting roughness greater than that of the surface of the SiC layer, thereby encouraging mechanical anchoring of said first coating. In addition, alumina has better physicochemical affinity with silicon than with SiC, and thus better adhesion. In addition, the good match between the coefficients of expansion of silicon and of SiC serves to minimize mechanical stresses at the silicon/SiC interface during thermal stressing. Thus, the interface between the part and the coating withstands high temperatures better, and the strain gauge remains secured to the part that presents deformations at high temperatures that are to be measured. Consequently, it is possible to take more reliable measurements of the deformations of the part on which the gauge is fastened.

BRIEF DESCRIPTION OF THE DRAWING

The invention can be better understood and its advantages appear more clearly on reading the following detailed description of an implementation given by way of non-limiting example. The description refers to the accompanying drawing, in which.

MORE DETAILED DESCRIPTION

Figure 1A:
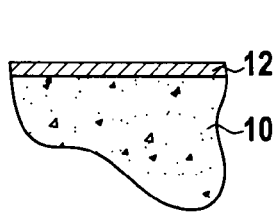
FIGS. 1A, 1B, and 1C show the steps of the method of the invention applied to a substrate covered in a layer of SiC.

FIG. 1A shows a part for use in very high temperature applications, having a substrate 10 that is covered in a layer 12 of silicon carbide (SiC). By way of example, the substrate 10 is made of a ceramic matrix composite material, or of a self-healing ceramic matrix composite material. The composite material may be SiC or it may be formed by a plurality of refractory ceramic layers that are precursors of glass in the silicon boron carbon (Si—B—C) ternary system. Such composites are reinforced, for example, by fibers made of carbon or ceramic. In applications to aviation turbomachines, such parts are typically thin parts, of frustoconical or plane rectangular shape, and they present a size of the order of a few hundreds of millimeters.

The SiC layer 12 deposited on the substrate is deposited, for example, by the technique known as chemical vapor deposition.

Figure 1B:
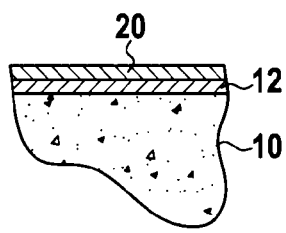

FIG. 1B shows the same part in which the SiC layer 12 is covered in a silicon adhesion underlayer 20 deposited on said SiC layer by vacuum plasma spraying (VPS). The vacuum plasma spraying technique is known, so only its major principles are mentioned herein. Vacuum plasma spraying is a thermal spraying technique using a blown arc plasma torch, and it is performed in an enclosure filled with argon at low pressure (i.e. less than atmospheric pressure). It consists in introducing the material for deposition into a very high energy jet (a plasma jet), the material being introduced in powder form (i.e. in the form of particles, here having a mean diameter of a few tens of micrometers). The particles are then melted by the jet and simultaneously accelerated towards the part for coating. These particles thus become flattened on the surface of the part in the form of droplets, which solidify very quickly after impact by their heat being conducted away, thereby forming platelets on the surface of the part. The stacking of these platelets perpendicularly to the surface of the part leads progressively to the deposit being built up. The speed of growth of the coating is of the order of 100 micrometers ($\mu m$) per minute.

By way of example, it is possible to use silicon powder having grain size in the range 5 $\mu m$ to 25 $\mu m$, which powder is sprayed in an enclosure where the pressure is 120 millibars, by means of a plasma torch with a plasma generating mixture (gas for facilitating plasma deposition) comprising argon with 15% to 20% by volume of hydrogen, and at a power of 40 kilowatts (kW) to 45 kW, onto the surface for coating that has been preheated to 750° C. The silicon adhesion underlayer may have a thickness lying in the range 50 $\mu m$ to 70 $\mu m$.

Figure 1C:
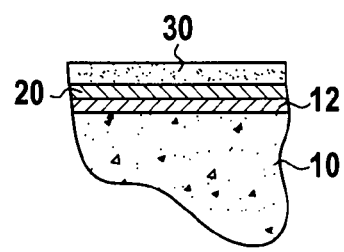

FIG. 1C shows the same part as FIG. 1B, on which a coating 30 of alumina $Al_2O_3$ has been deposited.

This coating 30 is typically deposited by atmospheric thermal spraying. Deposition by atmospheric thermal spraying is generally preferred over depositing a cement, since a cement would tend to crack at high temperatures. Deposits made by atmospheric thermal spraying are more cohesive and tenacious. "Thermal spraying" denotes a group of surface coating methods in which fine particles of the material for deposition are deposited in a molten or semi-molten state on the substrate. Atmospheric thermal spraying can be plasma spraying or flame spraying. Those two techniques are known, so only their general principles are summarized below.

The plasma spraying technique is a thermal spraying technique using a blown arc plasma torch that consists in introducing into a very high energy jet (a plasma jet), the material for deposition in powder form (i.e. in the form of particles, the particles having a mean diameter of a few tens of micrometers). The particles are then melted by the jet and simultaneously accelerated towards the part for coating. The particles thus flatten against the surface of the part in the form of droplets that solidify very quickly after impact by their heat being conducted away, thereby forming platelets on the surface of the part. Stacking these platelets perpendicularly to the surface of the part causes the deposit to be built up progressively. The spraying is performed at atmospheric pressure in air. The speed of growth of the coating is of the order of 100 micrometers ($\mu m$) per minute.

The flame spraying technique consists in introducing into the flame of an oxyacetylene torch a wire (rod) of the material that is to be sprayed onto the surface of the part. The material is then melted, atomized into fine particles that are accelerated towards the part for coating, and they flatten on the surface thereof in the form of droplets that solidify very quickly after impact by their heat being conducted away, thereby forming platelets on the surface of the part. Stacking these platelets causes the deposit to be built up progressively. Spraying is formed in air at atmospheric pressure. The speed of growth of the coating is fast (of the order of 100 $\mu m$ per minute).

Tests have been carried out by the Applicant on parts with a ceramic matrix composite substrate having a layer of SiC and a silicon adhesion underlayer deposited by vacuum plasma spraying, and on the same part without the adhesion underlayer. The silicon adhesion underlayer had a thickness of about 70 $\mu m$. All of the parts were subsequently coated in alumina by flame spraying. Thermal fatigue testing (for 60 cycles, each cycle corresponding to: temperature rise to 1100° C., temperature maintained for one hour at 1100° C., cooling in air down to 300° C.) shows that the part with the silicon adhesion underlayer did not present any trace of delamination at the SiC/alumina interface, unlike the parts without the adhesion underlayer.

The parts obtained by the method of the invention are typically used in aviation turbomachines, and are constituted, for example, by nozzle flaps, mixers, and combustion chamber elements.

In accordance with the invention, a device is made for measuring deformation on a part constituted by a substrate on which an SiC layer had been deposited by chemical vapor deposition (by way of example, the substrate could be made of one of the ceramic composites mentioned above). The measurement device comprises a free filament strain gauge used for measuring deformations of the part.

Figure 2:
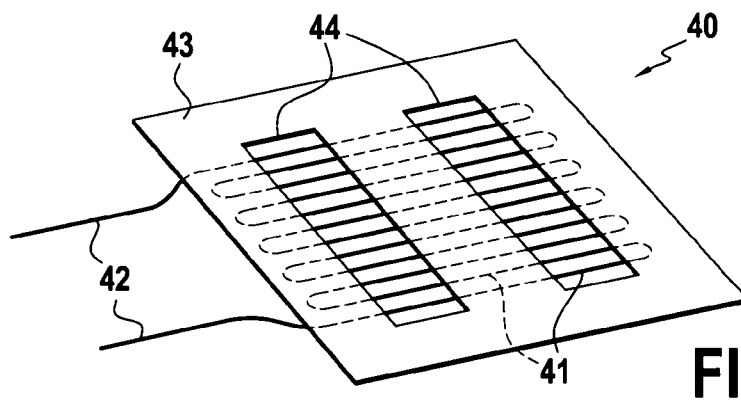
FIG. 2 is a perspective view of a strain gauge on its support.
Figure 3:
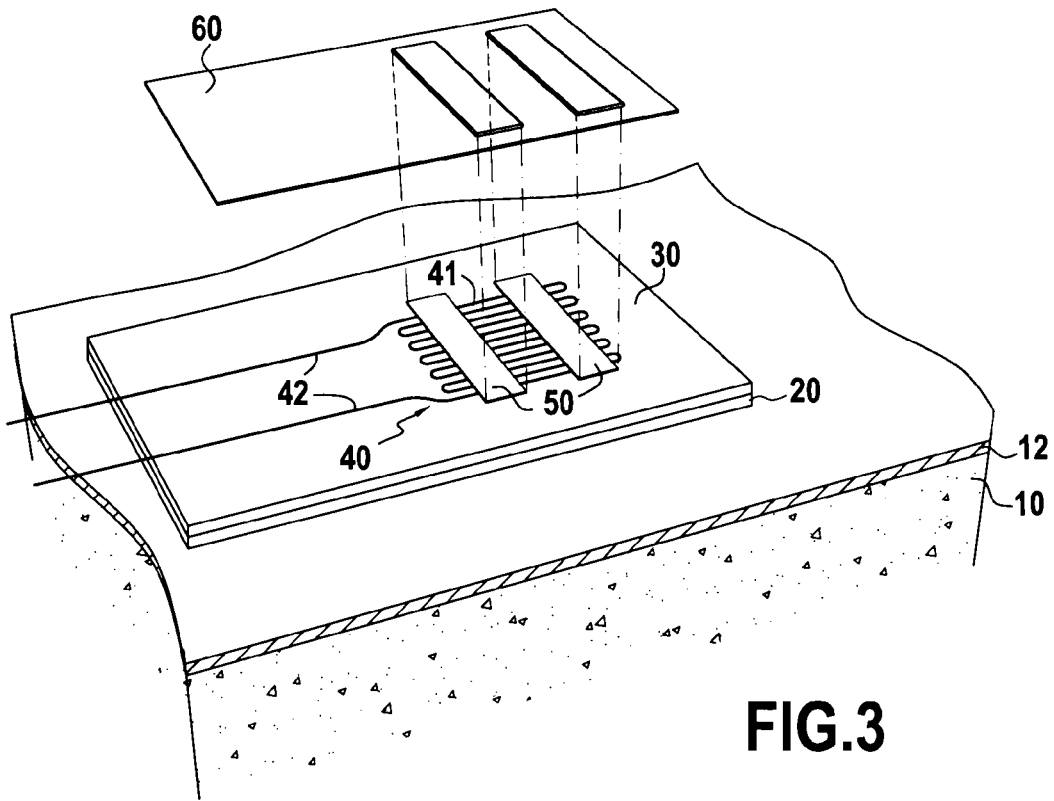
FIG. 3 is an exploded perspective view of a device of the invention for measuring deformation.

FIG. 2 shows a free filament strain gauge 40. Such a strain gauge is known to the person skilled in the art, and only its general structure is summarized below. The strain gauge 40 comprises a filament that is accordion-shaped as follows: the filament is folded back along itself a first time to form a U-shape of given height, then it is folded back a second time to form a second U-shaped situated in the same plane of the first U-shape and having limbs of the same length, but the other way up. The filament is thus curved back along itself numerous times using the same process, while ensuring that the limbs of the U-shape do not touch, so as to form a grid 41 in a plane. The limbs of consecutive U-shapes thus constitute strands of the grid 41, which strands are mutually parallel. The grid 41 is generally rectangular in shape, and is extended on one side by two filament ends 42 extending respectively from the first limb of the first U-shape and from the last limb of the last U-shape of the grid 41. The ends 42 are substantially parallel and lie in the same plane as the grid 41. The strain gauge also comprises a support 43. Typically the support 43 is an adhesive ribbon on which the grid 41 is stuck. The support 43 thus enables the configuration of the grid 41 to be maintained while the strain gauge 40 is being handled, in particular so as to keep the loops of the U-shapes in place together with the strands constituting the grid 41 so that the strands do not touch (so as to avoid a short circuit in the filament). The support 43 has a rectangular shape that extends beyond the grid 41 so that only the ends 42 of the filament extend beyond the support 43. The support 43 is oriented in such a manner that two of its sides are parallel to the strands of the grid 41, and its other two sides are perpendicular thereto. The ends 42 of the filament are connected to electrical equipment for passing an electric current along the filament, so as to measure in real time variations in the electrical resistivity of the filament, and thus deformations of the part on which it is fastened. When the part deforms in the direction of the strand forming the grid 41, the filament is stretched or caused to contract, and its electrical resistivity varies accordingly. It is for the purpose of increasing measurement sensitivity that the filament is folded back several times along itself to form a grid 41 as described above. Two rectangular openings 44 are cut out in the support 43 so that their long dimensions extend perpendicularly to the strands forming the grid 41. The openings 44 are long enough to reveal all of the strands of the grid 41 in these openings. The width of the openings 44 (in the strand direction) is limited so as to cover only a small fraction of the surface defined by the grid 41. Thus, the major fraction of the length of the filament constituting the grid 41 remains stuck to the support 43. One of the openings 44 is situated towards the end of the grid 41 that is closer to the filament end 42, and the other opening 44 is situated towards the other end of the grid 41.

The filament of the strain gauge 40 is made of a metal alloy, e.g. a nickel chromium (Ni—Cr) alloy, an iron-chromium-aluminum (Fe—Cr—Al) alloy, or a platinum-tungsten (Pt—W) alloy. By way of example, the diameter of the filament is 18 μm in the grid 41, and 76 μm in the ends 42.

The device for measuring deformation of the part is made as follows: the SiC layer 12 (previously deposited on the substrate 10 of the part by chemical vapor deposition) is initially coated in an adhesion underlayer 20 of silicon by vacuum plasma spraying, as mentioned in the description of FIG. 1B. Thereafter, a first alumina coating 30 is deposited on a portion of the adhesion underlayer 20 by atmospheric thermal spraying (plasma spring or flame spraying). For example, it is possible to use alumina powder with a grain size lying in the range 22 μm to 45 μm, which powder is projected by means of a plasma torch using a mixture of argon with 30% by volume of hydrogen and at a power of 45 kW. The roughnesses of the silicon layer provide good adhesion for the first alumina coating 30 on said layer.

Thereafter, the strain gauge 40 is placed on the first coating 30 of alumina, with the support 43 being above the grid 41. In this example the first coating 30 of alumina serves to insulate the strain gauge 40 from the substrate. The gauge 40 is held in place by the support 43 and a second coating 50 of alumina similar to the first is deposited on the grid 41 through the windows 44. The second coating 50 is likewise deposited by atmospheric thermal spraying. This second layer 50 is thus in the form of two rectangular strips, each having area equal to the area of one of the windows 44 and deposited in the location of one of said windows 44. The second coating 50 is thus directly in contact with the filament of the grid 41, and holes of filament on the first coating 30. It is then possible to remove the support 43, the grid then being held in place by the second coating 50. Thereafter, a third coating 60 of alumina (similar to the first two coatings) is deposited by atmospheric thermal spraying so as to cover the second coating 50, the portions of the grid 41 that are not covered by the second coating 50, and a portion of the ends 42. The two tips of the ends 42 are not covered by the third coating 60 so as to allow them to be connected to a source of electricity for measuring the deformation of the filament of the grid 41. By way of example, the first coating has a thickness of 100 μm, the second coating has a thickness of 50 μm, and the third coating has a thickness of 100 μm.

The second coating 50 and the third coating 60 together constitute an additional alumina coating that holds the strain gauge 40 on the first coating 30, the strain gauge 40 thus being embedded in the alumina of the first coating 30 and of the additional coating. Because of the roughnesses in the SiC layer, the alumina block constituted by the first coating 30 and the additional coating is secured to the part, even at the high temperatures (300° C. to 1100° C.) to which the part is subjected in operation (e.g. in an aviation turbomachine). Thus, deformation of the part is properly transmitted to the alumina block, and thus to the filament of the strain gauge 40, which enables accurate measurements to be taken of the deformation of the part.

The above-described method of depositing the strain gauge 40 on the first layer 30 is given by way of example, the principle being the same for depositing any other free filament strain gauge, providing that, at the end of the deposition method, the filament of the strain gauge 40 is embedded in the alumina block that is constituted by the first coating 30 and by the additional coating.

The method of making a coating on a substrate having its surface made of SiC, as described in the present invention, also covers circumstances in which the coating is made on a solid SiC part.

What is claimed is:

1. A method of making a device for measuring deformation, the method comprising the following steps:
   a) depositing, on a silicon carbide surface of a part constituted by a substrate covered in a silicon carbide layer deposited by chemical vapor deposition, a silicon adhesion underlayer by vacuum plasma spraying;
   b) depositing on said silicon adhesion underlayer an alumina coating by atmospheric thermal spraying;
   c) placing a free filament strain gauge on said coating, the gauge being held on a support, and said support possessing openings;
   d) depositing a second alumina coating on said strain gauge and on said coating by atmospheric thermal spraying through said openings;
   e) removing said support; and
   f) depositing a third alumina coating by atmospheric thermal spraying on said first coating, on said second coating, and on said strain gauge.

2. The method according to claim 1, wherein the adhesion underlayer has a thickness of 50 µm to 70 µm.

3. The method according to claim 1, wherein the atmospheric thermal spraying is selected between plasma spraying and flame spraying.

4. The method according to claim 1, wherein said substrate is selected between a composite material having a silicon carbide matrix and a composite material having a self-healing ceramic matrix.

* * * * *